United States Patent

Marchini et al.

[11] Patent Number: 5,830,262
[45] Date of Patent: Nov. 3, 1998

[54] GAS CHROMATOGRAPH OVEN WITH IMPROVED REGULATION OF THE AIR TEMPERATURE

[75] Inventors: Giovanni Marchini, Ghedi; Enzo Montagner, Pioltello; Giovanni Ostan, Milan, all of Italy

[73] Assignee: ThermoQuest Italia S.p.A., Italy

[21] Appl. No.: 855,954

[22] Filed: May 14, 1997

[30] Foreign Application Priority Data

May 16, 1996 [IT] Italy .................................. MI96U0367

[51] Int. Cl.⁶ .................................................. B01D 15/08
[52] U.S. Cl. ........................ 96/105; 73/23.36; 73/23.42; 96/101
[58] Field of Search .............................. 73/23.25, 23.26, 73/23.36, 23.42; 95/82, 87; 96/101–107

[56] References Cited

U.S. PATENT DOCUMENTS

| | | | |
|---|---|---|---|
| 3,165,147 | 1/1965 | Roof et al. ............................ | 96/102 X |
| 3,165,149 | 1/1965 | Raible et al. ......................... | 96/102 X |
| 3,224,499 | 12/1965 | Reinecke .............................. | 96/102 X |
| 3,309,504 | 3/1967 | Rosso et al. .......................... | 96/104 X |
| 3,422,603 | 1/1969 | Redmond, Jr. ........................ | 96/103 |
| 4,038,055 | 7/1977 | Varano et al. ......................... | 96/102 |
| 4,050,911 | 9/1977 | Welsh .................................. | 55/197 |
| 4,181,613 | 1/1980 | Welsh et al. .......................... | 210/179 |
| 4,286,456 | 9/1981 | Sisti et al. ............................ | 73/23.1 |
| 4,556,103 | 12/1985 | Kuwa et al. ........................... | 165/122 |
| 4,771,628 | 9/1988 | Sisti et al. ............................ | 96/101 X |
| 4,869,876 | 9/1989 | Arfman et al. ........................ | 422/89 |
| 4,908,488 | 3/1990 | Park .................................. | 219/10.55 R |
| 5,236,668 | 8/1993 | Higdon ................................ | 96/104 X |
| 5,298,225 | 3/1994 | Higdon ................................ | 96/104 X |
| 5,338,514 | 8/1994 | Morabito et al. ..................... | 96/105 X |
| 5,634,961 | 6/1997 | Gordon ............................... | 96/102 X |
| 5,656,170 | 8/1997 | Henderson ........................... | 96/102 X |
| 5,686,655 | 11/1997 | Itoi .................................... | 96/104 X |

FOREIGN PATENT DOCUMENTS

| | | | |
|---|---|---|---|
| 2921358 | 12/1980 | Germany ............................ | 96/102 |
| 82/01662 | 5/1982 | WIPO . | |
| WO 82/01661 | 5/1982 | WIPO ................................. | 96/101 |

*Primary Examiner*—Robert Spitzer
*Attorney, Agent, or Firm*—Millen, White, Zelano & Branigan, P.C.

[57] ABSTRACT

A gas chromatography oven is endowed with a shutter for the influx of air from the outside and a pair of shutters for the controlled outflow of air from the oven, the shutters being positioned on the rear wall of the oven, near the corners of the rear wall. On the upper wall of the oven, at least one injector of the sample to be analyzed and at least one detector are lodged in a removable drawer.

15 Claims, 2 Drawing Sheets

# GAS CHROMATOGRAPH OVEN WITH IMPROVED REGULATION OF THE AIR TEMPERATURE

BACKGROUND OF THE INVENTION

The present invention relates to a gas chromatography oven endowed with means for regulating the temperature of the air inside the oven in an accurate way, through the controlled influx and outflow of external air.

FIELD OF THE INVENTION

It is known that, during the chromatographic analysis of a mixture of compounds, it is necessary to maintain accurate control of the temperature to which the column is subjected during the various phases of the analysis. In particular, such temperature control must be maintained during heating and cooling of the column.

Techniques are known in the art for regulating the temperature of a gas chromatography oven, in some operational phases, by circulating in the oven a flow of air withdrawn from the outside.

The American Patent U.S. Pat. No. 4,181,613 describes, in one of its form of embodiment, a gas chromatography oven in which there is provision for a shutter for the influx of external air at ambient temperature and a shutter for the outflow of hot air to the outside. Both shutters are on the rear of the oven and the influx shutter conveys the air to a fan. There is a screen in front of the fan which divides the oven into a portion containing the capillary column(s) for the analysis and one containing the fan. The screen, furthermore, supports electric resistances for the heating of the air in the oven. With the shutters open, the fan provides for mixing the cold air with the hot air of the oven before it reaches the column. In this embodiment however the mutual disposition of the blades of the fan, the shutters and the heating resistances of the air doesn't allow perfect uniformity of temperature to be reached in all the flow streams of air that arrive at the column.

American Patent U.S. Pat. No. 4,286,456 describes a gas chromatography oven in which the blades of the fan are arranged around a nucleus containing means for heating the air. Though offering better uniformity of temperature to the air in the oven, this solution also presents the problem of not being able to regulate the temperature with precision and uniformity in the cooling phase.

More in general, the solutions of the known art are neither able to ensure a flow of air at uniform temperature onto the column during the cooling phase, nor the most constant flow possible particularly when the cooling must be at low speed, i.e. when there is a small ratio between variation of temperature and interval of time in which said variation takes place.

Another problem is that of maintaining the temperature of the capillary column constant or varying slowly; which is especially difficult when the column is near ambient temperature, for instance 50°–60° C.

In all these situations, in fact, the automatic opening of the outflow shutter, following a signal received from a suitable thermostat sensor, generally reduces the temperature much too rapidly to below the desired value, which causes the influx shutter to close and initiates automatic heating of the oven which then temporarily exceeds the desired temperature. This phenomenon generates a series of beats, i.e. much too frequent opening and closing of the shutters which create irregularity in the desired course of the temperature of the air.

OBJECTS OF THE INVENTION

The object of the present invention is to solve the aforementioned problems by means of a gas chromatography oven that provides means for accurately controlling the influx of external air at ambient temperature and the outflow of hot air from the gas chromatograph, giving a flow of air at uniform temperature onto the capillary column, also during the cooling phase.

Another object of the invention is to avoid irregularity in the flow of cold air in conditions of low speed cooling or of temperature maintenance, above all near ambient temperature.

SUMMARY OF THE INVENTION

Such objects are achieved through the present invention which relates to a gas chromatography oven, of the type comprising a thermally insulated cavity, defined by a front wall, a rear wall and four side walls and divided into a first portion, containing at least one gas chromatography column and into a second portion containing means for ventilation and means for heating the air, characterized by the rear wall comprising a shutter for the influx of air from the outside and a pair of shutters for the controlled outflow of air from the oven, said outflow shutters being located near the corners of said rear wall, particularly near the lower corners.

According to a preferred aspect of the present invention, the oven is further characterized by providing means for controlling thermostatically the partial or complete opening of one alone or both of the pair of outflow shutters.

According to a further aspect of the present invention, the oven is characterized by at least one injector of the sample to be analyzed and at least one detector, being lodged in a removable drawer on the outside of the upper wall of said oven. The drawer is complete with all the necessary connections for the operation of the injector and the detector and is anchored to the external structure of the oven.

The gas chromatography oven according to the present invention offers the advantage in the first place of giving a flow of air at uniform temperature onto the capillary column in all phases of the gas chromatography analysis.

Furthermore, the oven allows a regulated, substantially constant flow of external air, even with elevated shutter control of this external air. In fact, according to requirements, it is possible to open the exit shutters automatically, or open only one of said shutters, either completely or partially. That is particularly advantageous when the oven must undergo a cooling or a heating operation to temperatures near the ambient temperature, or when a controlled low speed cooling must take place.

BRIEF DESCRIPTION OF THE DRAWINGS

Further advantages and characteristics of the invention will become more evident from the following description, which is of illustrative and not limitative nature, with reference to the enclosed schematic drawings, in which.

DESCRIPTION OF THE PREFERRED EMBODIMENTS

Figure 1:
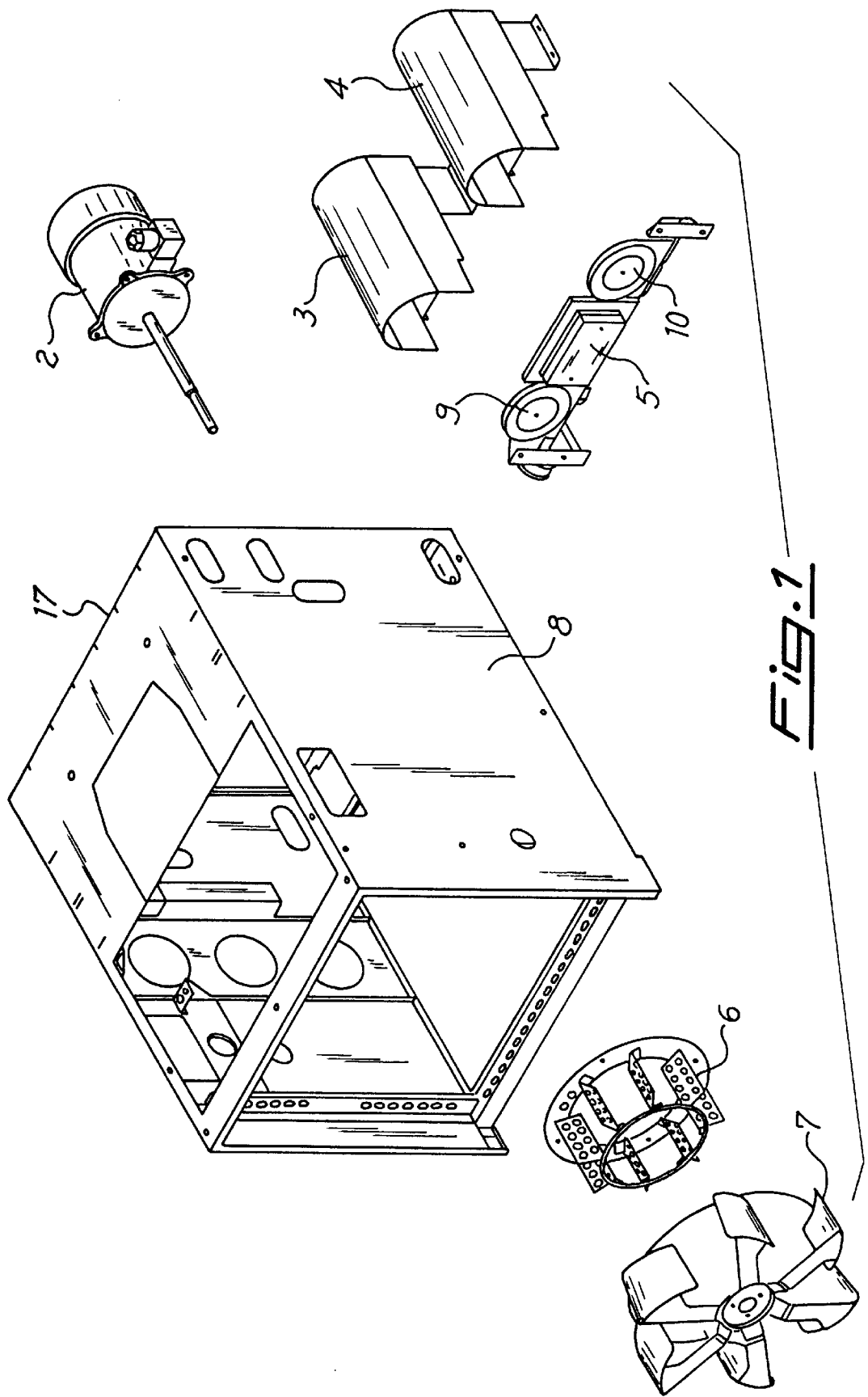
FIG. 1 is an exploded view in perspective of some components of a gas chromatography oven according to the present invention.

In FIG. 1 are shown the components that cooperate to allow the accurate regulation of the temperature inside the gas chromatography oven according to the present invention. In particular, it is shown element 8 which forms a thermally insulated cavity, defined by a front wall, a rear wall and four side walls. Also shown are a fan 7 and its related motor 2, a support 6 that can house a plurality of electric resistances, a pair of outflow shutters 9 and 10, an influx shutter 5 and two screening elements 3 and 4.

Figure 2:
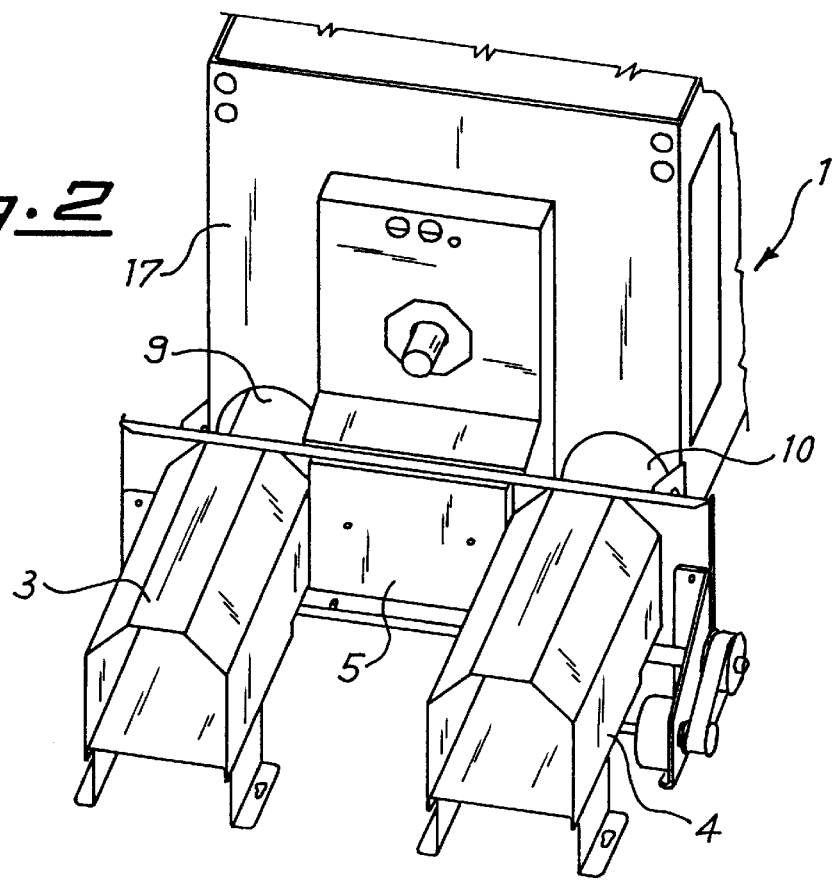
FIG. 2 is a view in perspective of the rear part of the gas chromatography oven.

In FIG. 2 is shown the rear part 17 of the oven 1 in correspondence of which are set the two outflow shutters 9 and 10 and the influx shutter 5. The screening elements 3 and 4 are applied In proximity of the openings of the shutters 9 and 10.

Figure 3:
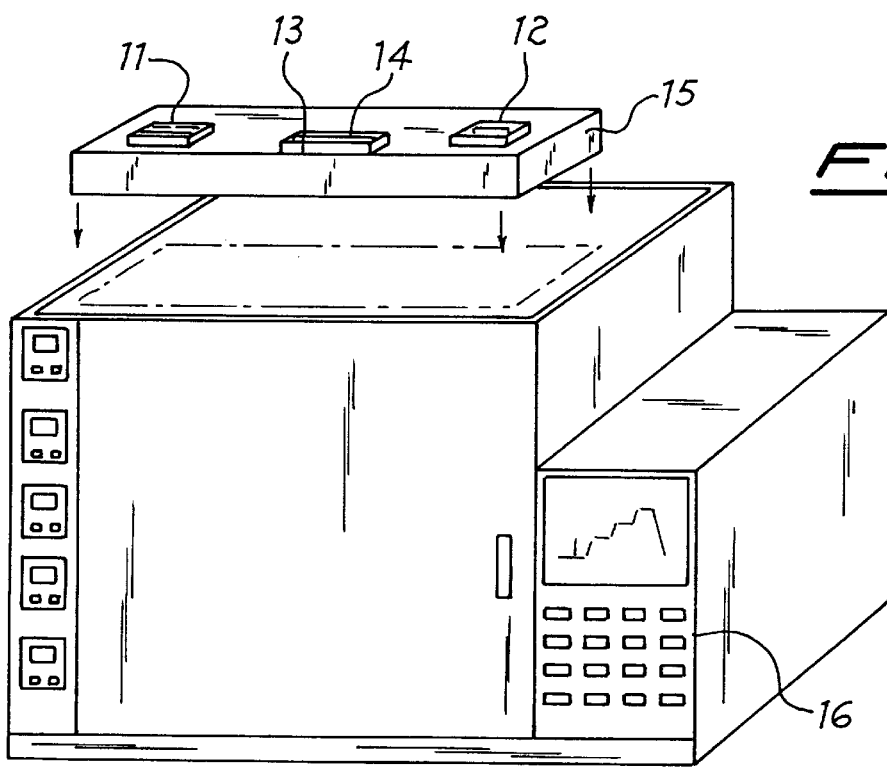
FIG. 3 is a view in perspective of the front part of the gas chromatography oven.

In FIG. 3 the oven 1 is shown, endowed with control unit 16, and provided on the upper side with a removable drawer 15 which houses the injectors 11 and 12 of the sample to be analyzed and the detectors 13 and 14.

The gas chromatography oven 1 is divided by an internal shield (not shown) into a first portion, containing at least one capillary column for chromatography, and a second portion containing the fan 7 and the electric resistances fitted onto the support 6 for the heating of the air. The shield allows the passage of the flow of air between its edges and the side walls of the oven. The fan 7 is shaped in such a way that the blades surround the support 6 and the related resistances, allowing the creation of a flow of direct air toward the capillary column which is composed of fluid streams at substantially uniform temperature.

The shutter 5 and the shutters 9 and 10, on the rear part 17 of the oven 1, are equipped with means of thermostatically controlling their total or partial opening and closing. In particular, the shutter 5 is opened to allow the influx of air from the outside, while the pair of shutters 9 and 10 is used for the controlled outflow of air from the oven. In order to create a circulation of air between the outside and the inside of the oven, the shutter 5 and at least one of the shutters 9 and 10 are mechanically linked.

Whenever the outflow of the hot air from the oven 1 must be controlled with precision, the aforesaid means of thermostatically controlled opening and closing, are able to effect the opening, partial or complete, of only one shutter of the pair of outflow shutters 9 and 10. This prevents the setting up of the aforementioned beats because of continuous rapid sequence of openings and closings of the shutters.

The outflow shutters 9 and 10 are set in the corners, preferably in the lower corners of the oven where the speed of the air is lower and therefore the pressure is higher, which favors the outflow of the air.

The aforesaid system of control of the temperature of the inside air in the oven 1 is particularly advantageous in the cases in which cold air must be admitted. That happens particularly when low speed cooling of the capillary column must take place, or when a constant or slowly varying temperature near the ambient temperature must be sustained.

Furthermore, to each of the shutters 9 and 10, for the outflow of the air, a tubular screening element 3 and 4 is applied, whose purpose is to divert the flow of hot air away from the influx shutter 5 and from the apparatus connected with the oven in general.

The connections of the tubular screening elements 3 and 4 to the shutters 9 and 10 are not airtight. In this way a space is created that allows a layer of cold air to enter the inside of the tubular elements 3 and 4, which is useful in the cooling of the hot air that comes out of the oven when it works at higher temperatures.

The removable drawer 15 which houses the injectors of the sample to be analyzed 11 and 12 and the detectors 13 and 14 is located above the upper side of the oven and is separated from it by an insulator layer that prevents metal-metal contact of the drawer 15 with the wall of the oven. This thermal insulation between injectors, detectors and oven favors the precision of the temperature control.

The removable drawer 15 has the purpose, furthermore, of increasing the flexibility of employment of the oven, allowing the substitution and use of different types of injectors 11 and 12 and/or of detectors 13 and 14.

We claim:

1. A gas chromatography oven, comprising a thermally insulated cavity defined by a front wall, a rear wall and four side walls and divided by an internal shield into a first portion, containing at least one gas chromatography column, and a second portion containing means for ventilation and means for heating the air, characterized by said rear wall housing a shutter for the influx of air from the outside and a pair of shutters for the controlled outflow of air from the oven, said outflow shutters being located near the corners of said rear wall.

2. A gas chromatography oven according to claim 1, characterized by said corners of the rear wall, in which the shutters for the outflow of the air are set, being the lower corners.

3. A gas chromatography oven according to claim 2, characterized by the shutters for the outflow of the air being substantially circular in form and the shutter for the influx of the air being substantially rectangular in form and being located half-way between the shutters for the outflow.

4. A gas chromatography oven according to claim 3, characterized by a tubular screening element being applied to each of said pair of shutters for the outflow of the air, for diversion of the flow of hot air from the influx shutter.

5. A gas chromatography oven according to claim 4, characterized by there being an opening or fissure left between each outflow shutter and its related tubular screening element for the admission of external air drawn in by the outflow.

6. A gas chromatography oven according to claim 5, characterized by at least one injector of the sample to be analyzed and at least one detector being lodged in a drawer fitted removably to the outside of the upper wall of said oven and being anchored to the external structure of the oven.

7. A gas chromatography oven according to claim 1, characterized by the shutters for the outflow of the air being substantially circular in form and the shutter for the influx of the air being substantially rectangular in form and being located half-way between the shutters for the outflow.

8. A gas chromatography oven according to claim 7, characterized by a tubular screening element being applied to each of said pair of shutters for the outflow of the air, for diversion of the flow of hot air from the influx shutter.

9. A gas chromatography oven according to claim 8, characterized by there being an opening or fissure left between each outflow shutter and its related tubular screening element for the admission of external air drawn in by the outflow.

10. A gas chromatography oven according to claim 9, characterized by at least one injector of the sample to be analyzed and at least one detector being lodged in a drawer fitted removably to the outside of the upper wall of said oven and being anchored to the external structure of the oven.

11. A gas chromatography oven according to claim 1, characterized by a tubular screening element being applied to each of said pair of shutters for the outflow of the air, for diversion of the flow of hot air from the influx shutter.

12. A gas chromatography oven according to claim 11, characterized by there being an opening or fissure left between each outflow shutter and its related tubular screening element for the admission of external air drawn in by the outflow.

13. A gas chromatography oven according to claim 12, characterized by at least one injector of the sample to be analyzed and at least one detector being lodged in a drawer fitted removably to the outside of the upper wall of said oven and being anchored to the external structure of the oven.

14. A gas chromatography oven according to claim 1, characterized by providing means for thermostatic control for the opening, partial or complete, of one or both of said pair of outflow shutters, in correspondence with a partial opening of the influx shutter.

15. A gas chromatography oven according to claim 1, characterized by at least one injector of the sample to be analyzed and at least one detector being lodged in a drawer fitted removably to the outside of the upper wall of said oven and being anchored to the external structure of the oven.

* * * * *